United States Patent
Sasaki

(10) Patent No.: US 6,936,061 B2
(45) Date of Patent: Aug. 30, 2005

(54) SURGICAL OPERATION INSTRUMENT

(75) Inventor: Katsumi Sasaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 355 days.

(21) Appl. No.: 10/029,627

(22) Filed: Dec. 21, 2001

(65) Prior Publication Data

US 2002/0055758 A1 May 9, 2002

Related U.S. Application Data

(63) Continuation of application No. PCT/JP01/03400, filed on Apr. 20, 2001.

(30) Foreign Application Priority Data

Apr. 27, 2000 (JP) ......................................... 2000-128265

(51) Int. Cl.[7] .............................................. A61B 17/28
(52) U.S. Cl. ...................................... 606/205; 606/207
(58) Field of Search ................................ 606/205, 206, 606/207, 170, 174, 167, 138, 139, 140, 141, 142, 143, 144, 145

(56) References Cited

U.S. PATENT DOCUMENTS

| | | |
|---|---|---|
| 5,275,608 A | 1/1994 | Forman et al. |
| 5,314,445 A | 5/1994 | Heidmueller nee Degwitz et al. |
| 5,350,391 A | 9/1994 | Iacovelli |
| 5,520,678 A | 5/1996 | Heckele et al. |
| 5,618,294 A | 4/1997 | Aust et al. |
| 5,901,895 A | 5/1999 | Heaton et al. |
| 5,908,436 A | 6/1999 | Cuschieri et al. |
| 5,984,932 A * | 11/1999 | Yoon .......................... 606/147 |

* cited by examiner

*Primary Examiner*—Vy Bui
(74) *Attorney, Agent, or Firm*—Scully, Scott, Murphy & Presser

(57) ABSTRACT

The present invention is provided with a treatment section provided at the distal end of an insertion section insertable into a body cavity, and being openable/closable and rotatable from side to side and up and down, an operation section provided at the proximal end of the insertion section and being openable/closable and rotatable from side to side and upward or downward, and first to third driving rods which connect the treatment section and the operation section together and which can be advanced or retracted. The present invention is characterized in that the opening/closing operation of the first and second handles causes the advancing/retracting movement of the driving rod, thereby opening or closing the jaws of the treatment section, and in that the rotation of the operation section causes the advancing/retracting movement of the driving rod, thereby rotating the treatment section relative to the axis of the insertion section.

16 Claims, 11 Drawing Sheets

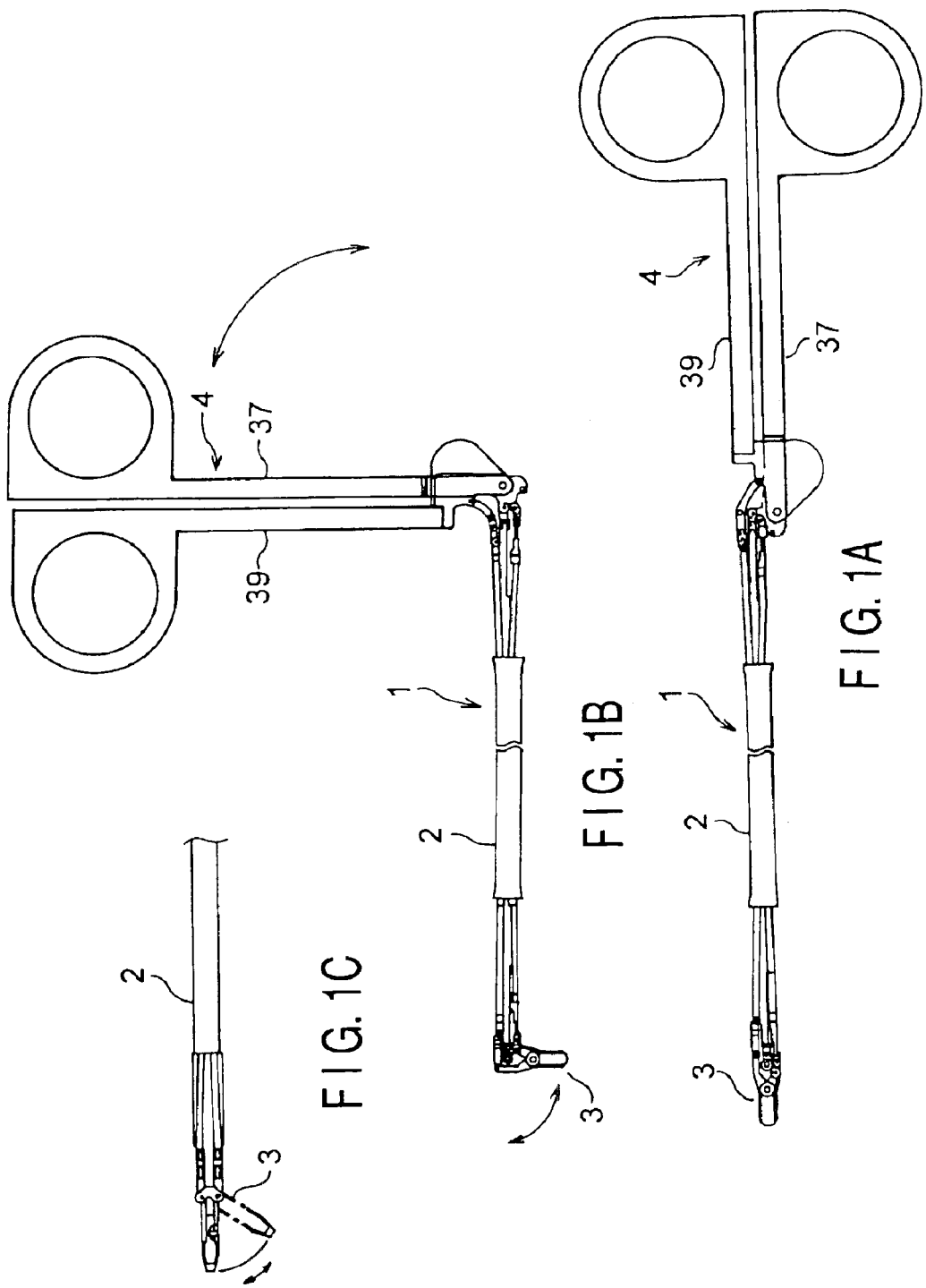

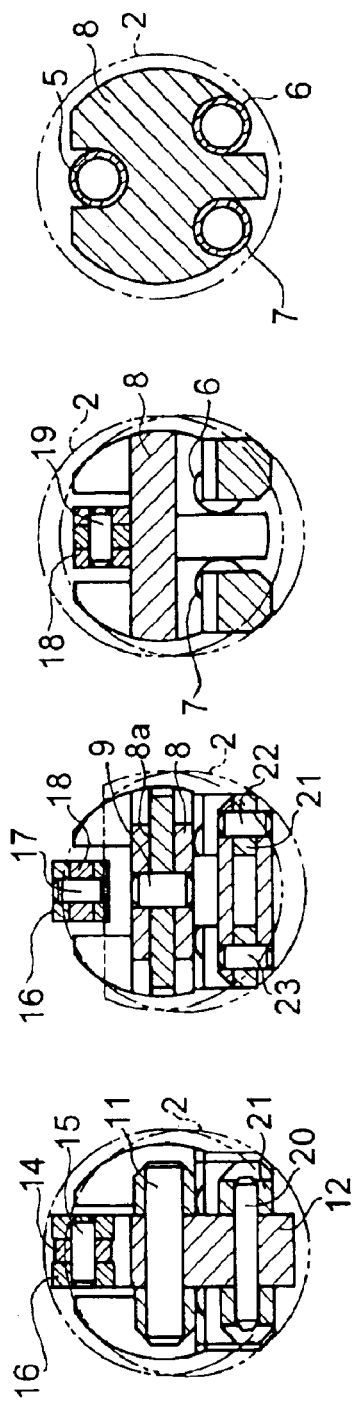
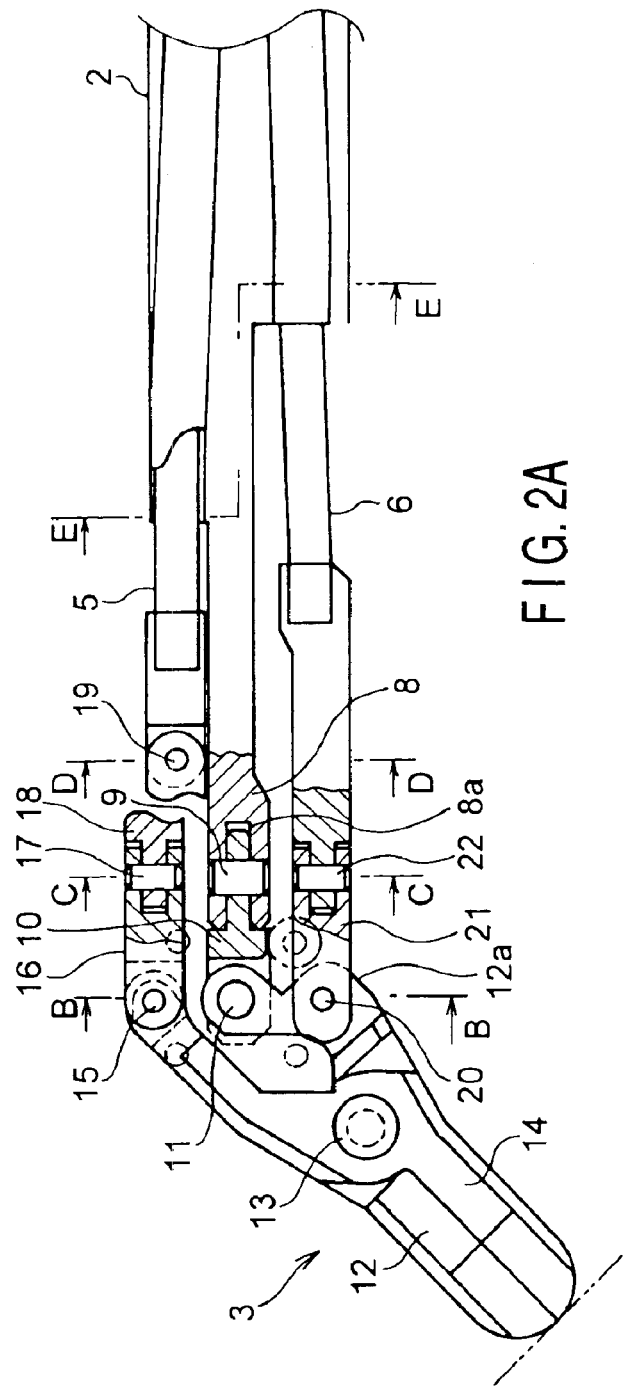
FIG. 2E
FIG. 2D
FIG. 2C
FIG. 2B
FIG. 2A

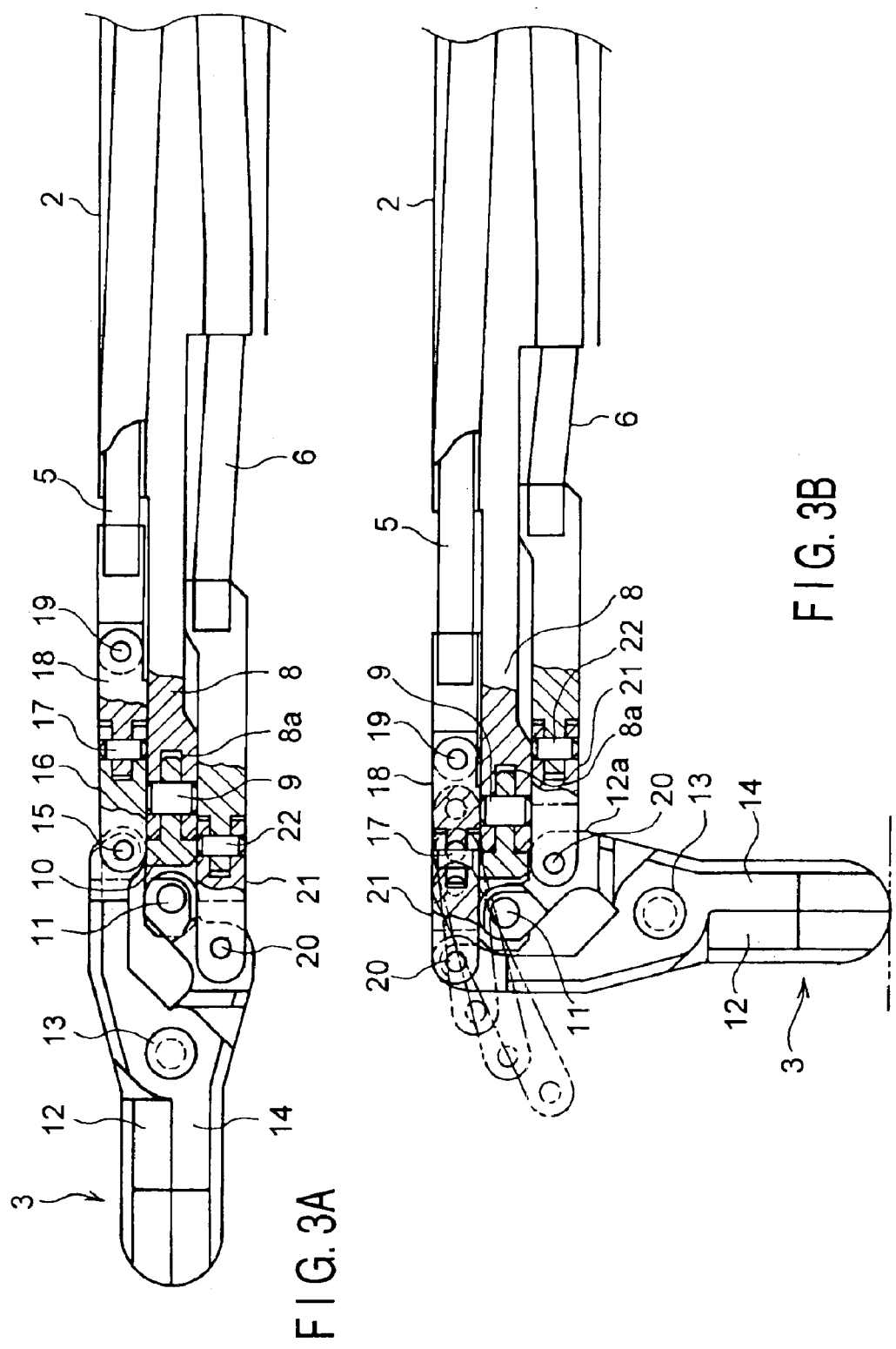

SURGICAL OPERATION INSTRUMENT

CROSS REFERENCE TO RELATED APPLICATIONS

This is a Continuation Application of PCT Application No. PCT/JP01/03400, filed Apr. 20, 2001, which was not published under PCT Article 21(2) in English.

This application is based upon and claims the benefit of priority from the prior Japanese Patent Application No. 2000-128265, filed Apr. 27, 2000, the entire contents of which are incorporated herein by reference.

BACKGROUND OF THE INVENTION

1. Field of the Invention

The present invention relates to a surgical operation instrument whose operation section, located at the proximal end of an insertion section, is gripped by the operator and whose treatment section, located at the distal end of the insertion section, is rotated and opened/closed, for surgical operation.

2. Description of the Related Art

As shown, for example, in U.S. Pat. No. 5,908,436, a surgical operation instrument comprises a shaft, an openable/closable treatment section located at the distal end of the shaft, and a handle located at the proximal end of the shaft and including a grip.

The grip is rotatably supported by the shaft. The grip is rotatable around two axes perpendicular to each other. The operator takes hold of the grip and rotates it around both the volar flexion axis of the wrist and the dorsal flexion axis of the wrist, without changing the position of the shaft.

The operator moves his or her wrist up and down or from side to side while holding the grip. In response to this, the treatment section can be rotated or opened/closed with no need to change the direction of the shaft.

The surgical operation instrument disclosed in U.S. Pat. No. 5,908,436 has problems in that the distance to the finger engagement portion is inevitably changed whenever the grip is held and the wrist is moved. Since the degree of finger engagement varies accordingly, the surgical operation instrument is not very easy to operate.

In the meantime, U.S. Pat. No. 5,275,608 discloses an instrument comprising a shaft, an openable/closable treatment section located at the distal end of the shaft, and a handle located at the proximal end of the shaft. The treatment section can be opened or closed, and is also designed to rotate its two elements in the same plane in response to an operation of the handle.

Although the surgical operation instrument of U.S. Pat. No. 5,275,608 allows a pair of treatment elements to rotate in the same plate in response to an operation of the handle, the range of rotation is narrow. Hence, suture and ligature cannot be executed with high efficiency.

An object of the present invention is to provide a surgical operation instrument in which the treatment section can be changed in direction by rotating the handle, without the insertion section being changed in direction, and which enables easy suture and ligature of tissues.

BRIEF SUMMARY OF THE INVENTION

The present invention comprises: a treatment section provided at the distal end of an insertion section insertable into a body cavity, and including a pair of jaws which are openable/closable and rotatable relative to the axis of the insertion section; an operation section provided at the proximal end of the insertion section and including handles which are openable/closable; and a driving rod which is revolvable around the axis of the insertion section and advanced or retracted in the axial direction of the insertion section. The present invention is characterized in that the opening/closing operation of the handles causes the advancing/retracting movement of the driving rod in such a manner as to open or close the jaws of the treatment section, and in that the rotation of the operation section causes the advancing/retracting movement of the driving rod in such a manner as to rotate the treatment section relative to the axis of the insertion section.

Also, the present invention comprises: a first coupling member provided at the proximal end of an insertion section insertable into a body cavity, and being rotatable on a first pivot in a first direction; handles provided for the first coupling member and rotatable on a second pivot in a second direction perpendicular to the first direction; a second coupling member provided for the handle; and a pair of driving rods connected to the second coupling member at positions sandwiching the second pivot. The present invention is characterized in that the handle is rotatable from side to side with the first pivot as a support point and is also rotatable up and down with the second pivot as a support point. When the handle is rotated from side to side relative to the first pivot, the paired driving rods move in opposite directions along the axis of the insertion section. When the handle is rotated up or down with the first pivot as a support point, the paired driving rods move in the same direction along the axis of the insertion section.

With the above structure, when the paired handles are rotated from side to side, the paired driving rods move in opposite directions along the axis of the insertion section. Since the treatment section rotates from side to side, it can be turned to intended positions. When the paired handles are rotated up or down, the paired driving rods move in the same direction along the insertion section. As a result, the treatment section can be rotated up or down. When the paired handles are opened or closed, the driving rods advance or retract, thereby opening or closing the paired jaws.

BRIEF DESCRIPTION OF THE SEVERAL VIEWS OF THE DRAWING

FIG. 1A is a side view showing the linear state of a surgical operation instrument according to the first embodiment of the present invention.

FIG. 1B is a side view showing the rotated state of the treatment section and operation section of the embodiment.

FIG. 1C is a view showing the lower portion of the distal end of the insertion section of the embodiment.

FIG. 2A is a longitudinal sectional view of the treatment section of the embodiment.

FIG. 2B is a sectional view taken along line B—B of the embodiment.

FIG. 2C is a sectional view taken along line C—C of the embodiment.

FIG. 2D is a sectional view taken along line D—D of the embodiment.

FIG. 2E is a sectional view taken along line E—E of the embodiment.

FIG. 3A is a side view illustrating the embodiment and showing a state where the treatment section is linearly held.

FIG. 3B illustrates the embodiment and is a side view showing a state where the treatment section is turned downward by 90°.

DETAILED DESCRIPTION OF THE INVENTION

Figure 1D:
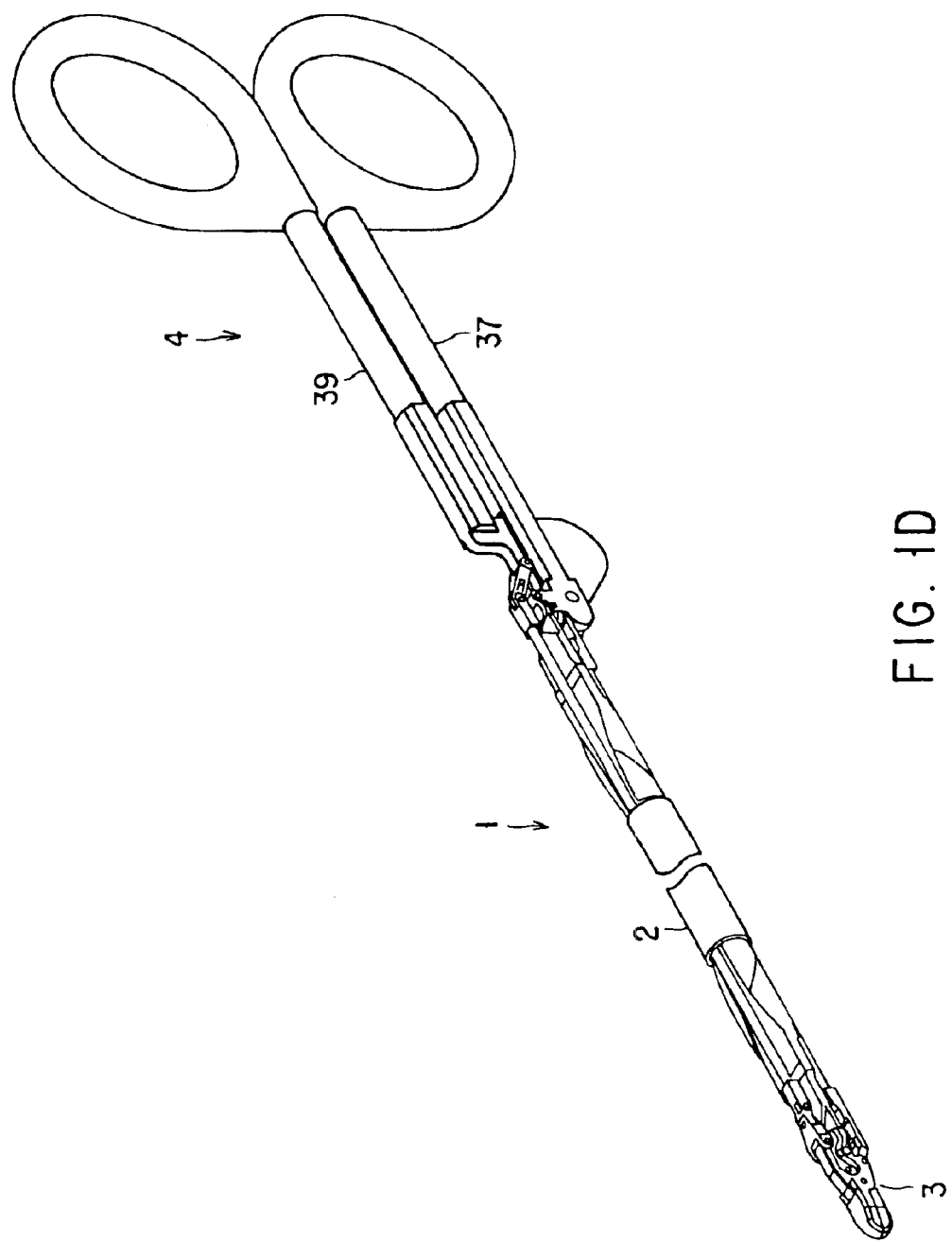
FIG. 1D is a perspective view showing the state in which the operation section and the treatment section are horizontal with reference to the insertion section of the embodiment.
Figures 1E, 1F:
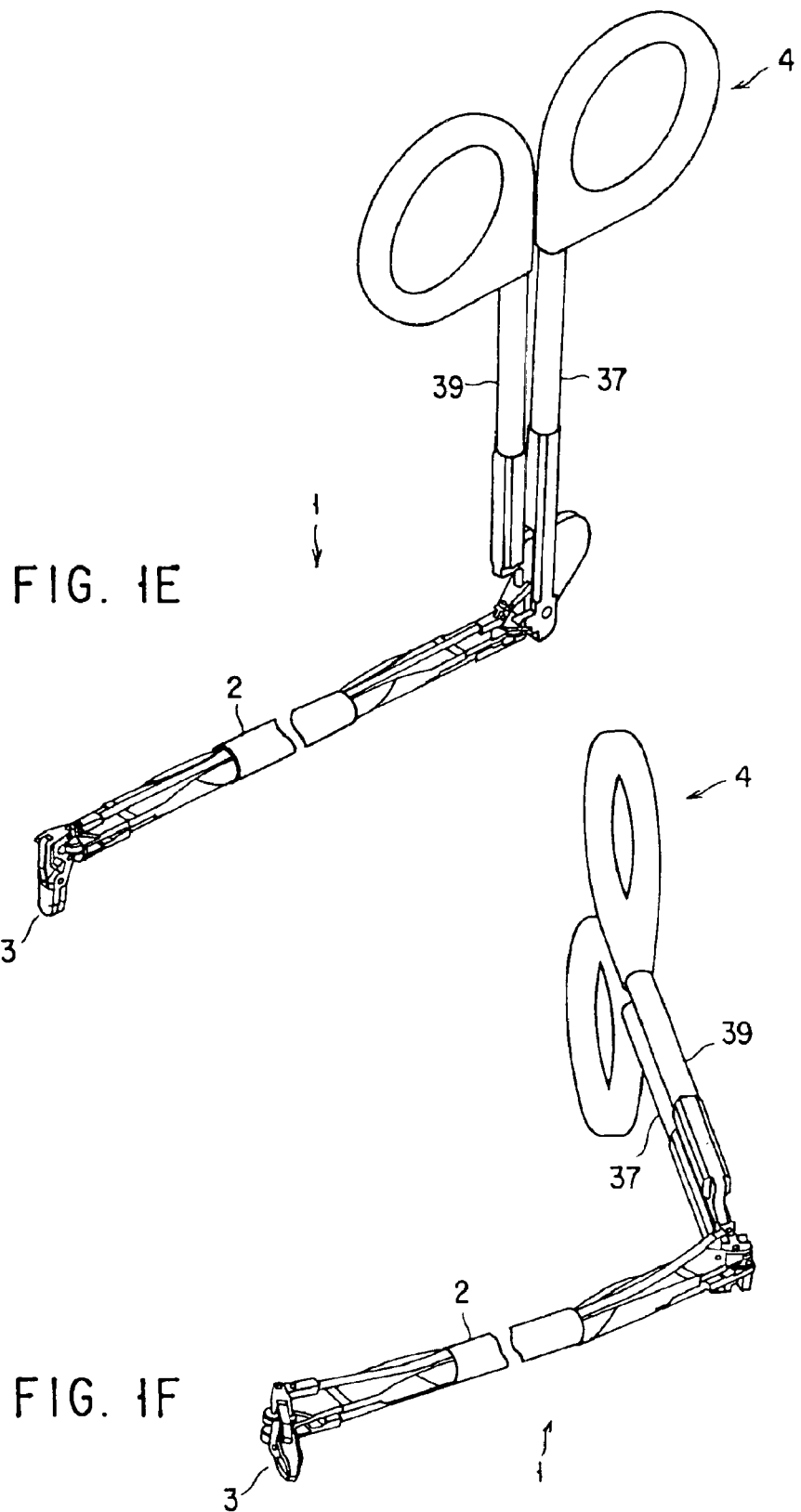
FIG. 1E is a perspective view showing the state where the operation section is turned vertically upward and the treatment section is turned vertically downward relative to the insertion section of the embodiment.
FIG. 1F is a perspective view showing the state where the operation section is turned leftward and the treatment section is turned rightward relative to the insertion section of the embodiment.
Figure 1G:
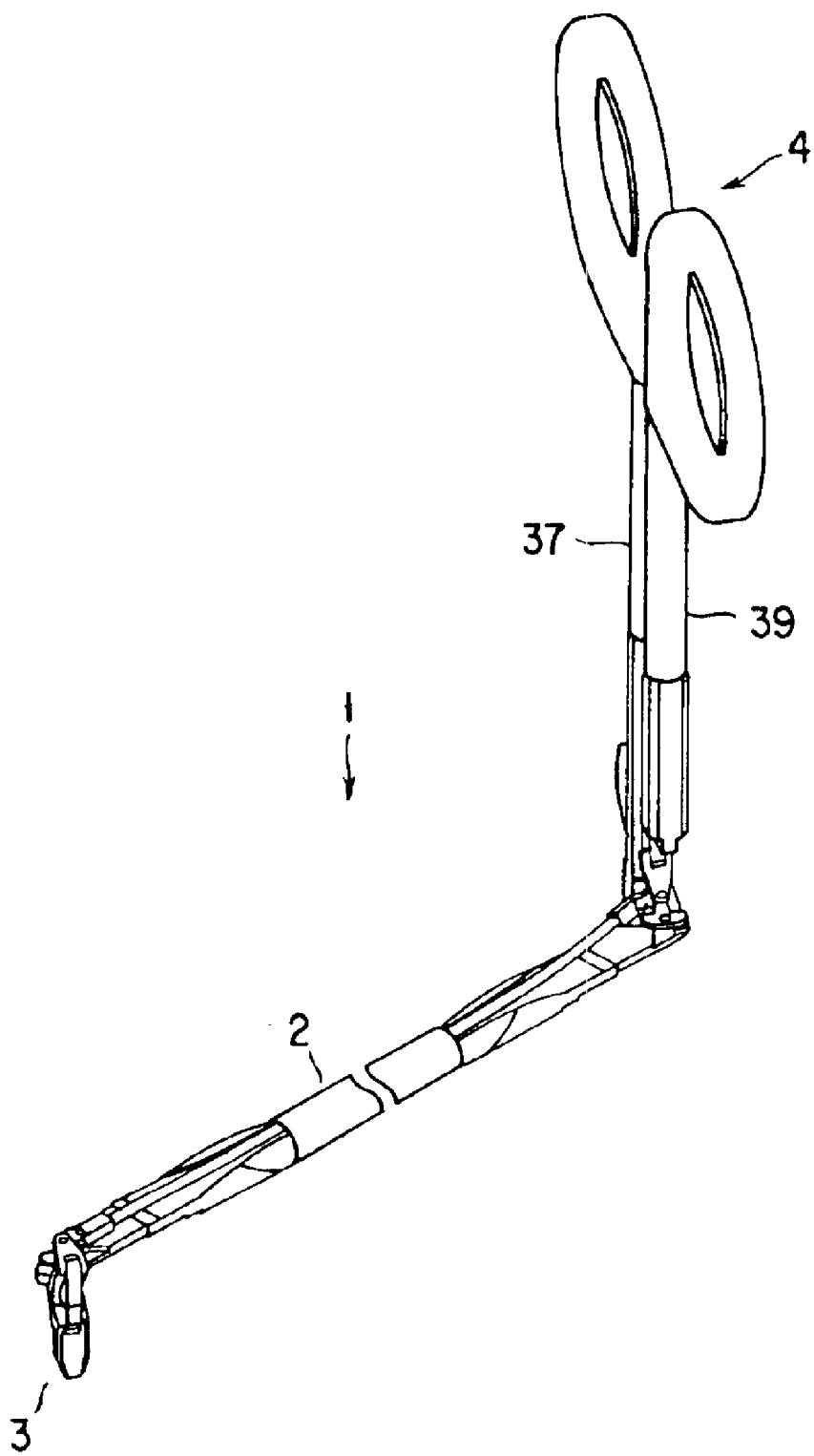
FIG. 1G is a perspective view showing the state where the insertion section is first turned vertically upward and then leftward relative to the insertion section of the embodiment, and where the treatment section is first turned vertically downward and then rightward relative to the insertion section.

FIG. 1A to FIG. 4 show the first embodiment. FIGS. 1A–1G show the entire structure of a surgical operation instrument. Of these Figures, FIG. 1A is a side view showing the linear state, FIG. 1B is a side view showing how a treatment section and an operation section are rotated, FIG. 1C is a view showing the lower portion of the distal end of the insertion section, FIG. 1D is a perspective view showing the state in which the operation section and the treatment section are horizontal relative to the insertion section of the embodiment, FIG. 1E is a perspective view showing the state where the operation section is turned vertically upward and the treatment section is turned vertically downward relative to the insertion section, FIG. 1F is a perspective view showing the state where the operation section is turned leftward and the treatment section is turned rightward relative to the insertion section, and FIG. 1G is a perspective view showing the state where the insertion section is first turned vertically upward and then leftward relative to the insertion section and where the treatment section is first turned vertically downward and then rightward relative to the insertion section.

A schematic structure of the surgical operation instrument will be described. As shown in FIGS. 1A to 1G, the surgical operation instrument 1 comprises an insertion section 2, a treatment section 3 provided at the distal end of the insertion section 2, and an operation section 4 provided at the proximal end of the insertion section 2.

Figure 4:
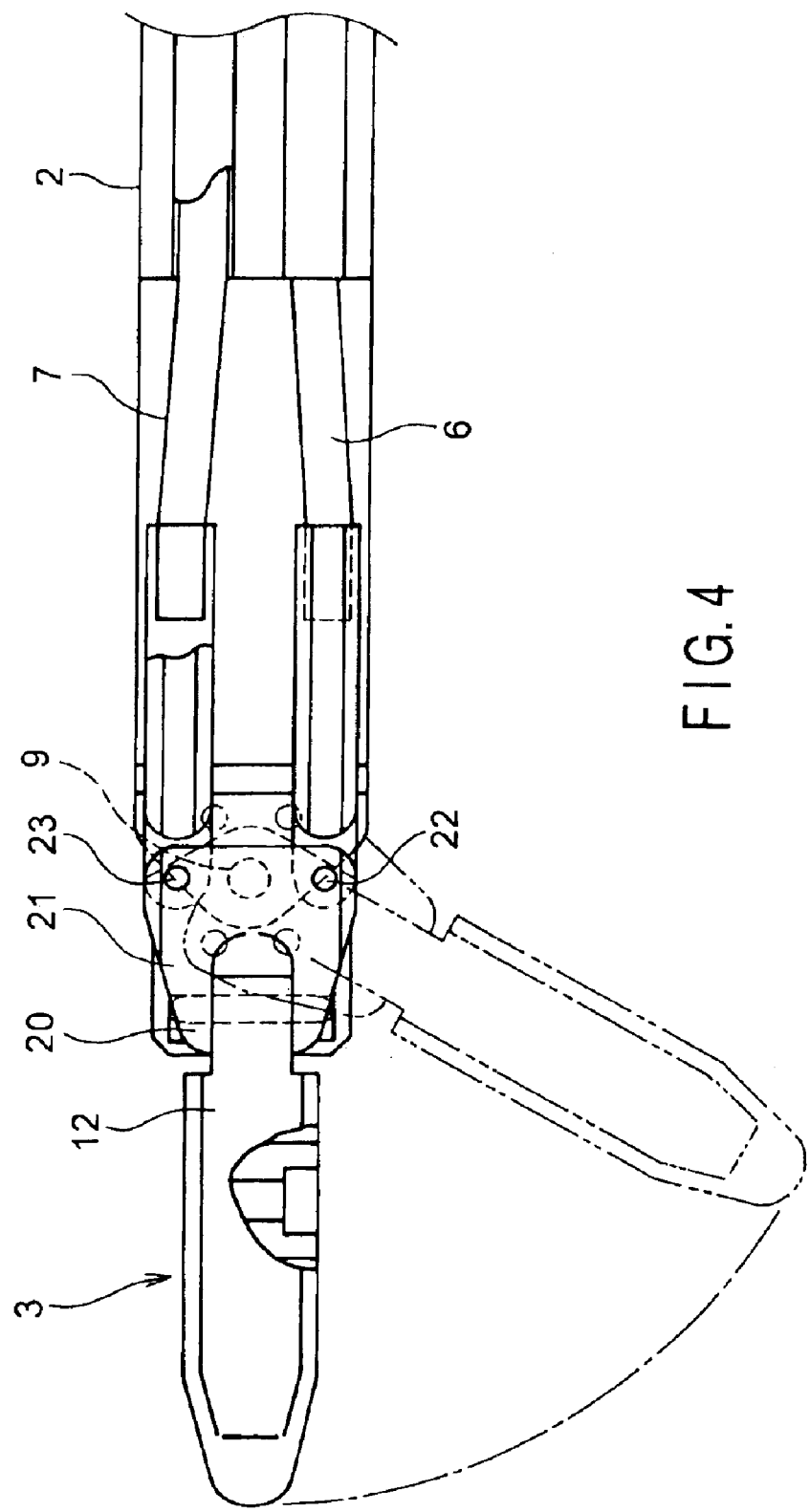
FIG. 4 illustrates the embodiment and is a plan view showing a state where the treatment section is rotated leftward.

The structure of the surgical operation instrument 1 will be described with reference to FIGS. 2A to 4. Of these Figures, FIG. 2A is a sectional view showing a state in which the treatment section is rotated downward by 45°, FIG. 2B is a sectional view taken along line B—B of FIG. 2A, FIG. 2C is a sectional view taken along line C—C of FIG. 2A, FIG. 2D is a sectional view taken along line D—D of FIG. 2A, FIG. 2E is a sectional view taken along line E—E of FIG. 2A, FIG. 3A is a side view showing a state where the treatment section 3 is linearly held, FIG. 3B is a side view showing a state where the treatment section is turned downward by 90°, and FIG. 4 is a plan view showing a state where the treatment section is rotated leftward.

As shown in FIGS. 2A to 4, the insertion section 2 is a long pipe with a small diameter. In the insertion section 2, a first driving rod 5, a second driving rod 6 and a third driving rod 7 extend in parallel to one another. The first driving rod 5 is shifted upward from the axis of the insertion section 2. The second and third driving rods 6 and 7 are shifted downward from the axis of the insertion section 2 and are symmetrical with each other. The second and third driving rods 6 and 7 can be advanced or retracted in the axial direction independently of each other.

The treatment section 3 will be described. The insertion section 2 has a rigid support portion 8 at the distal end thereof. The support portion 8 is integral with the insertion section 2 and protrudes frontward. The support portion has a slot 8a at the distal end. A rotating plate 10, which is allowed to rotate from side to side by a pivotal support shaft 9 extending perpendicular to the axial direction of the insertion section 2, is coupled to the slot 8a. A first pivotal pin 11 is fixed to the rotating plate 10 in a direction perpendicular to the pivotal support shaft 9. The first pivotal pin 11 rotatably supports the proximal portion of a first jaw 12. The proximal end of this first jaw 12 includes a curved portion 12a, and the second and third driving rods 6 and 7 are coupled to the curved portion 12a by use of means to be described later.

A second jaw 14 is rotatably coupled to the intermediate portion of the first jaw 12 by means of a second pivotal pin 13. The first jaw 12 and the second jaw 14 are rotatable relative to each other, with the second pivotal pin 12 as a support point. One end of a first coupling member 16 is rotatably coupled to the proximal end of the second jaw 14 by means of a first coupling pin 15, and the other end of the first coupling member 16 is coupled to a second coupling member 18 by means of a pivotal support pin 17. The other end of the second coupling member 18 is rotatably coupled to the distal end of the first driving rod 5 by means of a second coupling pin 19.

A third coupling member 21 is connected to the curved portion 12a of the first jaw 12 by means of a third coupling pin 20. The proximal end portion of the third coupling member is horizontally wide, and a fourth coupling pin 22 and a fifth coupling pin 23 are provided on this wide proximal end portion in such a manner that they are horizontally apart. The fourth coupling pin 22 is coupled to the second drive rod 6, and the fifth coupling pin 23 is coupled to the third driving rod 7.

The surgical operation instrument 1 of the above structure operates as follows. When the first driving rod 5 is advanced, the proximal end of the second jaw 14 is pushed forward by means of the first and second coupling members 16 and 18. As a result, the second jaw 14 rotates, with the pivotable support pin 11 as a support point, and the first and second jaws 12 and 14 open. Conversely, when the first driving rod 5 is retraced, the proximal end of the second jaw 14 is pulled backward by means of the first and second coupling members 16 and 18. As a result, the second jaw 14 rotates, with the pivotable support pin 11 as a support point, and the first and second jaws 12 and 14 close.

When the second and third driving rods 6 and 7 are retracted at the same time, the proximal end of the first jaw 12 is pulled backward by means of the third coupling member 21. The first jaw 12 rotates, with the first pivotal support pin 11 as a support point, and the second jaw 14 rotates in the same direction, with the first coupling pin 15 as a support point. The first and second jaws 12 and 14 can be rotated until they become substantially perpendicular to the axis of the insertion section 2. Conversely, when the second and third driving rods 6 and 7 are advanced at the same time, the proximal end of the first jaw 12 is pushed forward by means of the third coupling member 21. The first jaw 12 rotates, with the first pivotal support pin 11 as a support point, and the second jaw 14 rotates in the same direction, with the first coupling pin 15 as a support point. In this manner, the first and second jaws 12 and 14 can be simultaneously rotated from side to side relative to the axis of the insertion section 2. It should be noted that the proximal end of the support portion is cylindrical and is engageable with the distal end of the insertion section 2.

The first driving rod 5 can be advanced even if the first and second jaws 12 and 14 are not horizontal relative to the insertion section 2. In this case, the proximal end of the second jaw 14 is pushed forward by means of the first and second coupling members 16 and 18. As a result, the second jaw 14 rotates, with the second pivotal support pin 13 as a support point, and the first and second jaws 12 and 14 open.

Next, the second driving rod 6 is retracted, and the third driving rod 7 is advanced thereby. In response to this, the rotating plate 10 rotates leftward, with the pivotal support shaft 9 as a support point. As a result, the first and second jaws 12 and 14 rotate leftward, with the pivotal support shaft 9 as a support point, as indicated by the one-dot-dash line in FIG. 4. Conversely, when the second driving rod 6 is advanced, and the third driving rod 7 is retracted, the rotating plate 10 rotates rightward, with the pivotal support shaft 9 as a support point. As a result, the first and second jaws 12 and 14 rotate rightward, with the pivotal support shaft 9 as a support point.

According to the embodiment, the openable/closable first and second jaws 12 and 14 can be rotated up and down and from side to side. The first and second jaws 12 and 14 can be easily moved to a target location, thus ensuring a high degree of freedom in the treatment.

Figure 5A:
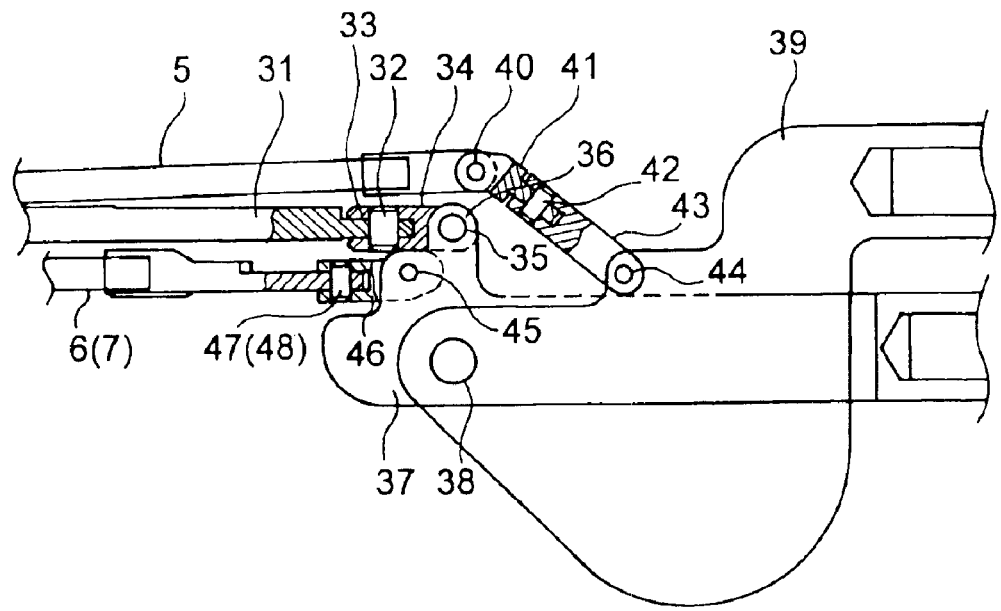
FIG. 5A illustrates the embodiment and is a side view showing a state where the treatment section is linear and first and second jaws are closed.
Figure 5B:
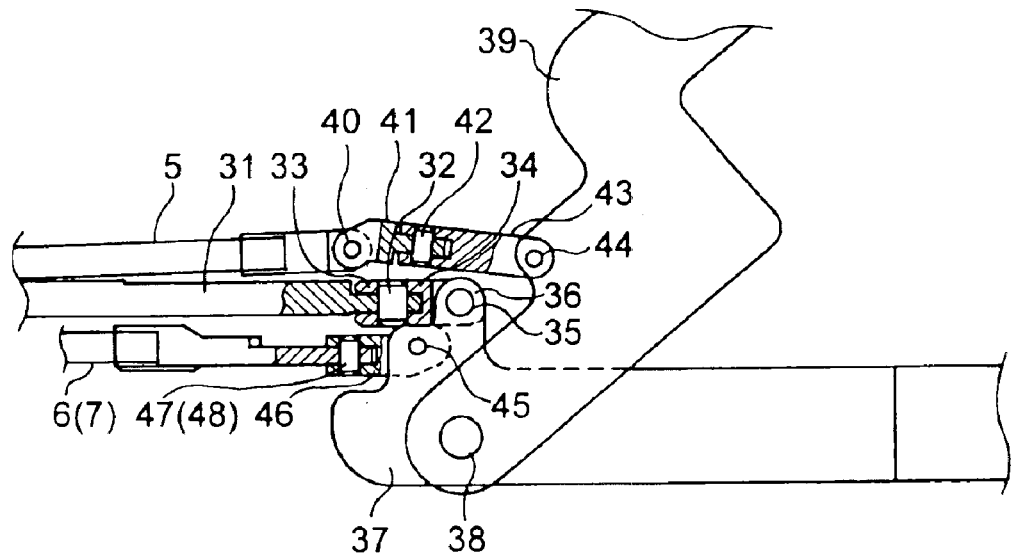
FIG. 5B illustrates the embodiment and is a side view showing a state where the treatment section is linear and the first and second jaws are open.
Figure 6A:
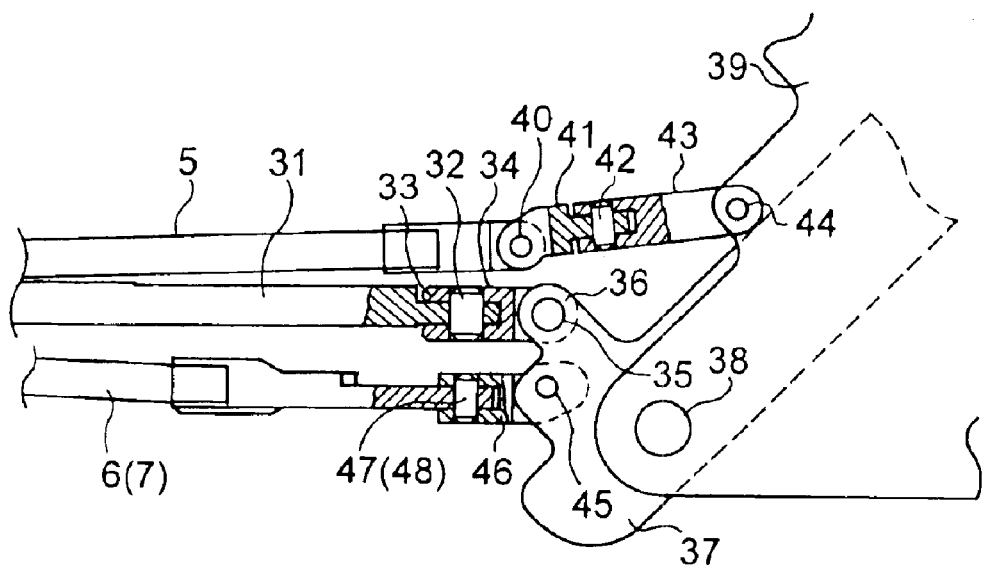
FIG. 6A illustrates the embodiment and is a side view showing a state where the treatment section is turned 45° and the first and second jaws are closed.
Figure 6B:
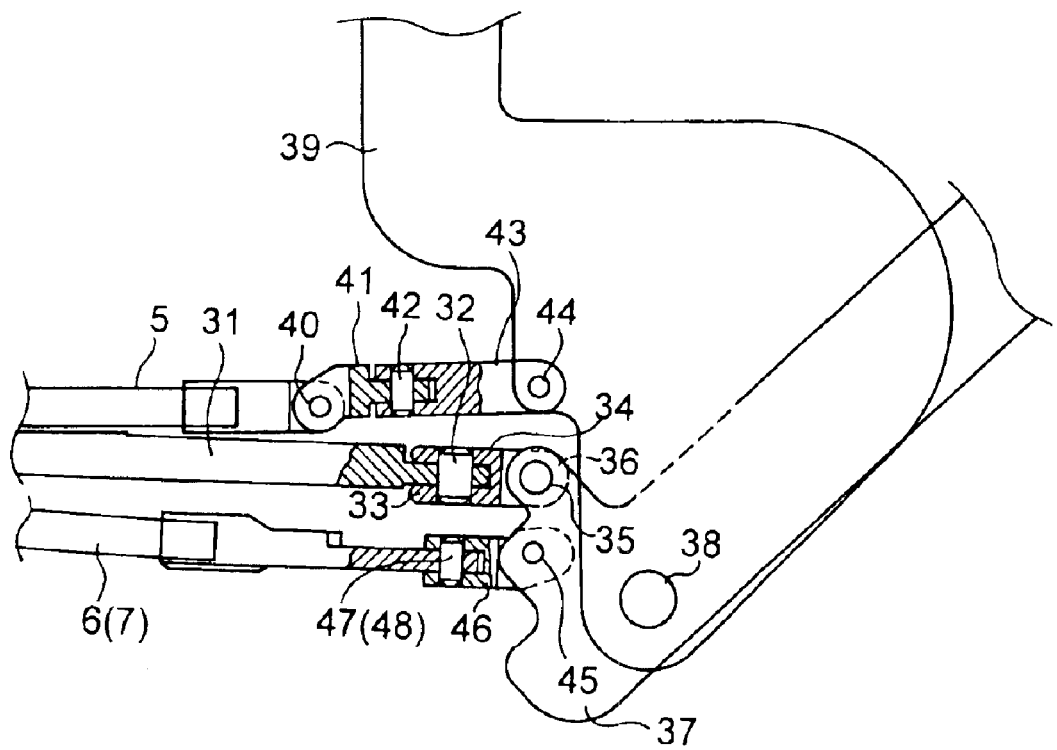
FIG. 6B illustrates the embodiment and is a side view showing a state where the treatment section is turned 45° and the first and second jaws are open.
Figure 7A:
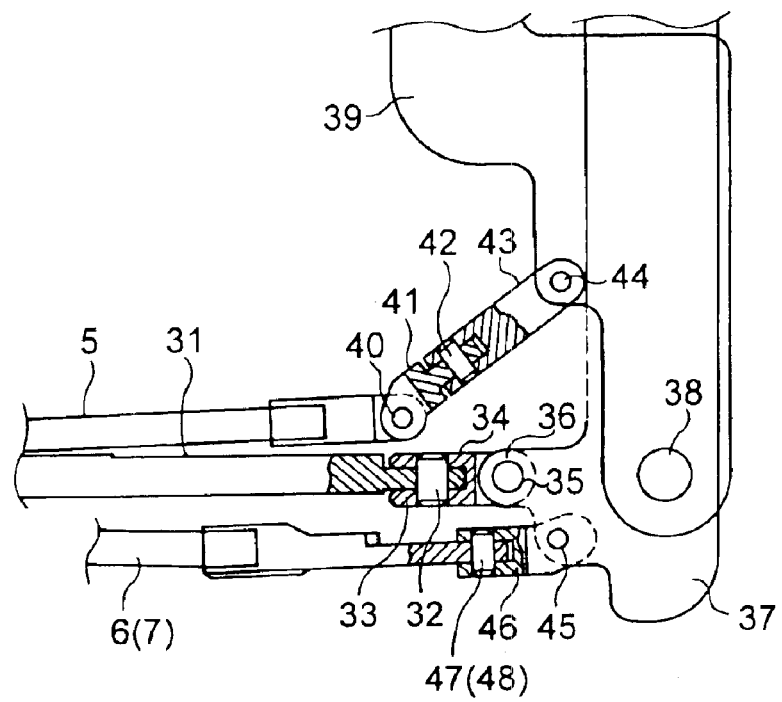
FIG. 7A illustrates the embodiment and is a side view showing a state where the treatment section is turned 90° and the first and second jaws are closed.
Figure 7B:
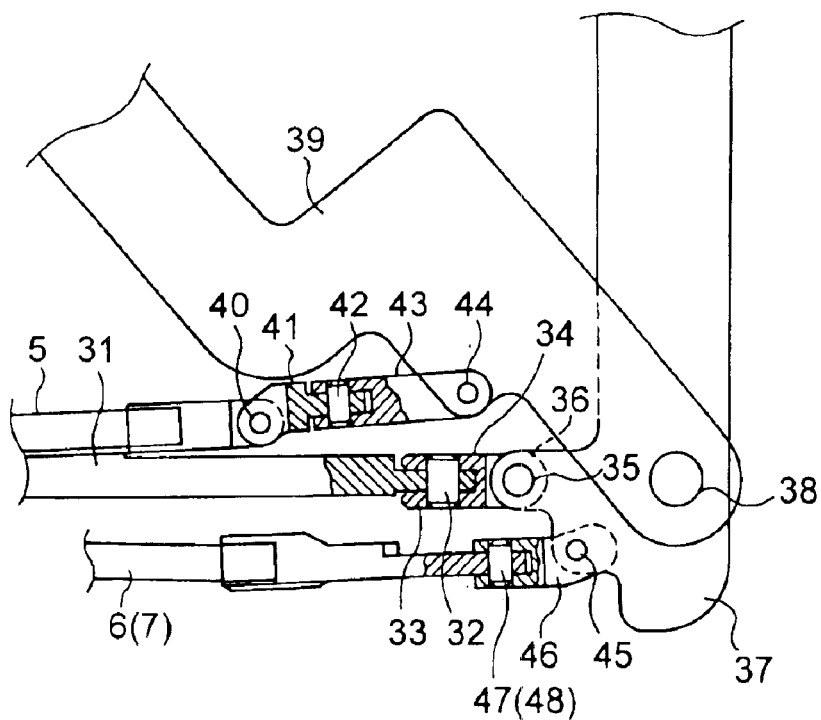
FIG. 7B illustrates the embodiment and is a side view showing a state where the treatment section is turned 90° and the first and second jaws are open.

The operation section 4 will now be described with reference to FIGS. 5A to 7B. FIG. 5A is a side view showing the operation section 4 which is in a state where the treatment section 3 is linear and first and second jaws 12 and 14 are closed. FIG. 5B is a side view showing the operation section 4 which is in a state where the treatment section 3 is linear and the first and second jaws 12 and 14 are open. FIG. 6A is a side view showing the operation section 4 which is in a state where the treatment section 3 is turned 45° and the first and second jaws 12 and 14 are closed. FIG. 6B is a side view showing the operation section 4 which is in a state where the treatment section 3 is turned 45° and the first and second jaws 12 and 14 are open. FIG. 7A is a side view showing the operation section 4 which is in a state where the treatment section 3 is turned 90° and the first and second jaws 12 and 14 are closed. FIG. 7B is a side view showing the operation section 4 which is in a state where the treatment section 3 is turned 90° and the first and second jaws 12 and 14 are open.

At the proximal end of the insertion section 2 as well, the first driving rod 5 is shifted upward from the axis of the insertion section 2, and the second and third driving rods 6 and 7 are shifted downward from the axis of the insertion section 2 and are symmetrical with each other. A support portion 31, which is rigid and protrudes rearward, is provided at the proximal end of the insertion section 2. The support portion 31 is provided with a first pivotal support portion 33 including a vertically-extending pivotal shaft 32. A first coupling member 34 is provided for the first pivotal support portion 33 to be rotatable from side to side.

The first coupling member 34 is provided with a second pivotal support portion 36 including a pivotal shaft 35 extending from side to side. A first handle 37 is provided for this second pivotal support portion 36 in such a manner as to be rotatable upward or downward. A second handle 39 is provided for the first handle 37 by means of a pivotal shaft 38 in such a manner that the second handle 39 is rotatable upward or downward.

A pivotal shaft 40 extending from side to side is provided for the proximal end of the first driving rod 5. A first coupling shaft 41 is coupled to the pivotal shaft 40 in such a manner that the first coupling shaft 41 is rotatable upward or downward. A vertically-extending pivotal shaft 42 is provided for the first coupling shaft 41. One end of a second coupling shaft 43 is coupled to the pivotal shaft 42 in such a manner as to be rotatable from side to side. The other end of the second coupling shaft 43 is coupled to a pivotal shaft 44 to be rotatable upward or downward. The pivotal shaft 44 extends from side to side and provided for the second handle 39.

A pivotal shaft 45 extending from side to side is provided at a lower level than the pivotal shaft 35 of the first handle 37. One end of a second coupling member 46 is coupled to the pivotal shaft 435 in such a manner as to be rotatable upward or downward. The other end of the second coupling member 46 is horizontally wide, and vertically-extending pivotal shafts 47 and 48 (only one of which is shown) are provided for the right and left ends of the horizontally wide portion. The second and third driving rods 6 and 7 are coupled to the pivotal shafts 47 and 48, respectively. Relative to the support portion 31 at the proximal end of the insertion section 2, therefore, the first and second handles 37 and 39 are rotatable from side to side, with the first pivotal support portion 33 as a support point, and are rotatable upward and downward, with the second pivotal support portion 36 as a support point.

The surgical operation instrument of the above structure operates as follows. When the second handle 39 is rotated away from the first handle 37, with the pivotal shaft 38 as a support point, the driving rod 5 advances. Since the proximal end of the second jaw 14 is pushed forward by means of the first and second coupling members 16 and 18, the second jaw 14 rotates, with the first pivotal support pin 11 as a support point. As a result, the first and second jaws 12 and 14 open. Conversely, when the second handle 39 is rotated toward the first handle 37, with the pivotal shaft 38 as a support point, the driving rod 5 retracts. Since the proximal end of the second jaw 14 is pulled backward by means of the first and second coupling members 16 and 18, the second jaw 14 rotates, with the first pivotal support pin 11 as a support point. As a result, the first and second jaws 12 and 14 close. It should be noted that the angle of rotation of the second handle 39 is substantially equal to the angle of rotation of the second jaw 14.

When the first handle 37 is rotated, with the pivotal shaft 35 as a support point, and the second and third driving rods 6 and 7 are retracted simultaneously, the proximal end of the first jaw 12 is pulled rearward by means of the third coupling member 21. Therefore, the first jaw 12 rotates, with the first pivotal support pin 11 as a support point. The second jaw 14 rotates in the same direction, with the first coupling pin 15 as a support point. The first and second jaws 12 and 14 can be rotated until they become substantially perpendicular to the axis of the insertion section 2. Conversely, when the first handle 37 is rotated, with the pivotal shaft 35 as a support point, and the second and third driving rods 6 and 7 are advanced simultaneously, the proximal end of the first jaw 12 is pushed forward by means of the third coupling member 21. Therefore, the first jaw 12 rotates, with the first pivotal support pin 11 as a support point. The second jaw 14 rotates in the same direction, with the first coupling pin 15 as a support point. The first and second jaws 12 and 14 can be rotated until they become substantially horizontal relative to the axis of the insertion section 2.

The first driving rod 5 can be advanced by rotating the second handle 39, with the pivotal shaft 38 as a support point, even if the first and second jaws 12 and 14 are not horizontal with reference to the insertion section 2. In this case, the proximal end of the second jaw 14 is pushed forward by means of the first and second coupling members 16 and 18. As a result, the second jaw 14 rotates, with the second pivotal support pin 13 as a support point, and the first and second jaws 12 and 14 open.

Next, the second driving rod 6 is retracted by rotating the first and second handles 37 and 39 rightward together, with the pivotal shaft 32 as a support point. Thereby, the third driving rod 7 is advanced. In response to this, the rotating plate 10 rotates leftward, with the pivotal support shaft 9 as a support point. As a result, the first and second jaws 12 and 14 rotate leftward, with the pivotal support shaft 9 as a support point, as indicated by the one-dot-dash line in FIG. 4. Conversely, the second driving rod 6 is advanced by rotating the first and second handles 37 and 39 leftward together, with the pivotal shaft 32 as a support point, and the third driving rod 7 is retracted, the rotating plate 10 rotates rightward, with the pivotal support shaft 9 as a support point. As a result, the first and second jaws 12 and 14 rotate rightward, with the pivotal support shaft 9 as a support point.

A description will be given of the operation of the surgical operation instrument of the above structure.

The second handle 39 can be rotated downward relative to the first handle 37 of the operation section 4, with the pivotal shaft 38 as a support point. When the second handle 39 has been rotated until the first and second coupling shafts 41 and 43 become parallel to each other, as shown in FIG. 5A, the first driving rod 5 is moved rearward toward the operation section 4 by means of the first and second coupling shafts 41 and 43.

The first coupling pin 15 is pulled toward the operation section 4 by means of the first coupling member 16 connected to the first driving rod 5 and located close to the treatment section 3. As shown in FIG. 3A, therefore, the first and second jaws 12 and 14 rotate, with the first pivotal support pin 11 as a support point. As a result, the first and second jaws close, and the instrument become linear as a whole.

As shown in FIG. 7A, the first and second handles 37 and 39 of the operation section 4 are rotated upward by 90°, with their parallel state maintained. As a result, the second and third driving rods 6 and 7 are retracted along the insertion section 2 by means of the second coupling member 46.

Therefore, the first coupling pin 15 is projected frontward by means of the first coupling member 16 connected to the first driving rod 5 and located close to the treatment section 3. As shown in FIG. 3B, the first and second jaws 12 and 14 are rotated downward by 90°, with the first pivotal support pin 11 as a support point, while maintaining their closed state. In this manner, the treatment section 3 can be made to linearly extend in the extension direction of the insertion section 2 or turned at an angle to the insertion section 2, by rotating up or down the first and second handles 37 and 39 of the operation section 4, with the pivotal shaft 35 as a support point. For example, FIG. 6A shows the state where the first and second handles 37 and 39 have been rotated 45°, with their parallel state maintained. In this state, the first and second jaws 12 and 14 are turned 45° downward, with their closed state maintained.

Even if the treatment section 3 is directed in any direction, the first and second handles 37 and 39 can be rotated rightward, with the pivotal shaft 32 as a support point. This rotation causes the second coupling member 46 to retract the second driving rod 6. As a result, the third driving rod 7 is advanced.

The fourth coupling pin 22 of the treatment section 3 is retracted, and the fifth coupling pin 23 is advanced. As a result, the third coupling member 21 rotates leftward, with the pivotal support shaft 9 as a support point, and the first and second jaws 12 and 14 rotate leftward (see FIG. 1B). Conversely, when the first and second handles 37 and 39 are rotated together leftward, with the pivotal shaft 32 as a support point, the second coupling member 46 causes the second driving rod 6 to advance and the third driving rod 7 to retract.

Therefore, the fourth coupling pin 22 of the treatment section 3 advances, and the fifth coupling pin 23 retracts. As a result, the third coupling member 21 rotates rightward, with the pivotal support shaft 9 as a support point, and the first and second jaws 12 and 14 rotate rightward.

In this manner, the first and second jaws 12 and 14 rotate leftward in response to the rightward rotation of the first and second handles 37 and 39. Since the first and second handles 37 and 39 and the first and second jaws 12 and 14 become substantially parallel, the treatment section 3 can be directed in an arbitrary direction by operating the first and second handles 37 and 39.

As shown in FIG. 5B, the second handle 39 of the operation section 4 is rotated upward, with the pivotal shaft 38 as a support point, in such a manner that the second handle 39 rotates relative to the first handle 37. When the first and second handles 37 and 39 are opened thereby, the first driving rod 5 is advanced by means of the second coupling shaft 43 and the first coupling shaft 41.

Therefore, the first coupling pin 15 is projected frontward by means of the first coupling member 16 connected to the first driving rod 5 and located close to the treatment section 3. Thus, the second jaw 14 opens relative to the first jaw 12, with the second pivotal support pin 13 as a support point. As shown in FIG. 6B, the second handle 39 of the operation section 4 is rotated upward relative to the first handle 37, with the pivotal shaft 38 as a support point. This rotation causes the second treatment section 3 to rotate 45°. When, in this state, the first handle 37 and the second handle 39 are opened, the first driving rod 5 is advanced by means of the first and second coupling shafts 41 and 43.

Therefore, the first coupling pin 15 is projected frontward by means of the first coupling member 16 connected to the first driving rod 5 and located close to the treatment section 3. Thus, the second jaw 14 opens relative to the first jaw 12, with the second pivotal support pin 13 as a support point. As shown in FIG. 7B, the second handle 39 of the operation section 4 is rotated upward relative to the first handle 37, with the pivotal shaft 38 as a support point. This rotation causes the second treatment section 3 to rotate 90°. When, in this state, the first handle 37 and the second handle 39 are opened, the first driving rod 5 is advanced by means of the first and second coupling shafts 41 and 43.

Since the first coupling pin 15 is projected frontward by means of the first coupling member 16 connected to the first driving rod 5 and located close to the treatment section 3, the second jaw 14 opens relative to the first jaw 12, with the second pivotal support pin 12 as a support point.

Figure 8A:
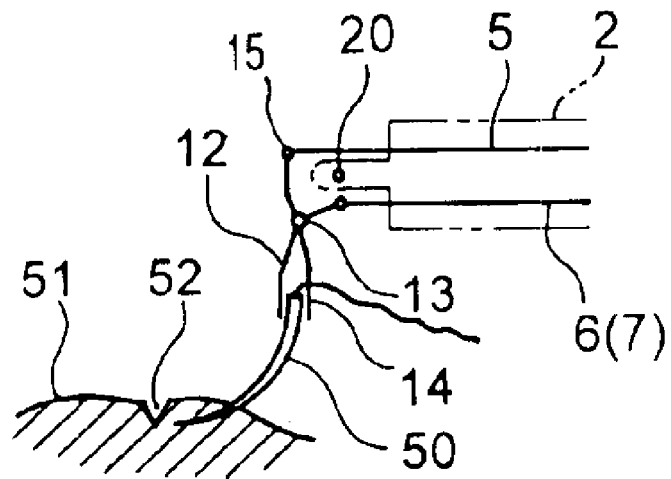
FIGS. 8A and 8B illustrate the embodiment and show how an operation instrument is used.

A description will now be given as to how incised portions of tissues are sutured. FIG. 8A shows a state where the first driving rod 5 is retracted, the first and second jaws 12 and 14 are rotated downward in such a manner that they are substantially perpendicular to the axis of the insertion section 2, and a suture needle 50 with a thread is taken hold of by use of the first and second jaws 12 and 14. In this state, the suture needle 50 is positioned in the vicinity of incised portions 51 of a tissue 51, and the distal end of the insertion section 2 is moved down to the tissue 51. In response to this movement, the suture needle 50 penetrates the tissue 51.

Figure 8B:
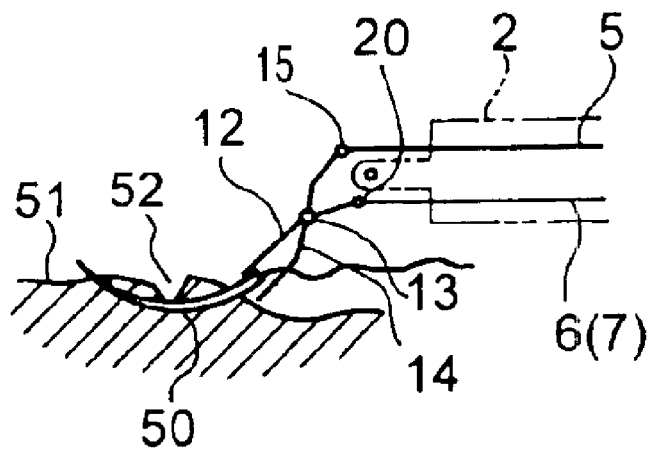

Next, the first driving rod 5 is retracted. Since the proximal end of the first jaw 12 is pulled then, the first and second jaws 12 and 14 rotate forward, with the first pivotal support pin 11 as a support point. As shown in FIG. 8B, the suture needle 50 goes through the tissue 51 having the incised portions 52, and the distal end of the suture needle 50 comes out of the surface layer of the tissue 51. In this manner, the first and second jaws 12 and 14 can be rotated in the axial direction of the suture needle 50, thus enabling easy penetration by the suture needle 50.

As described above, the first and second jaws 12 and 14 can be rotated for opening/closing in the state where they are directed in the axial direction of the insertion section 2 or in the state where they are rotated downward and directed in the direction substantially perpendicular to the axial direction of the insertion section 2. Hence, the first and second jaws 12 and 14 can reliably moved to a target location. In addition to the suture, the first and second jaws 12 and 14 can be used for clamping the tissue 51 or removing part of the tissue.

When the suture needle 51 is clamped with the first and second jaws 12 and 14 for suture, the first and second handles 37 and 39 are rotated from side to side, with the pivotal support portion 32 as a support point. As a result, the first and second jaws 12 and 14 can rotate from side to side. Even if the suture direction is at an angle to the axial direction of the insertion section 2, the suture can be continued without releasing the suture needle 50 or holding it again. In addition, the operation instrument 1 need not be inserted again from a different direction, which is a bothersome operation.

According to the surgical operation instrument of the present invention, the insertion section can be inserted into a body cavity of a living body, and a suture needle with a thread can be clamped by means of a pair of jaws, for suture or ligature of a living tissue.

As described above, according to the present invention, when the handles are opened or closed relative to each other, the driving rods are advanced or retracted in such a manner as to open or close the treatment section. When the handles are rotated, the driving rods are advanced or retracted in such a manner as to rotate the treatment section relative to the axis of the insertion section. Therefore, the treatment section can be turned in different directions by rotating the handles, and the direction of the insertion section remains unchanged in the meantime. Hence, suture and ligature of tissues can be executed with high efficiency.

What is claimed is:

1. A surgical operation instrument comprising:
   an elongate insertion section insertable into a body cavity and including distal and proximal end portions, the insertion section having an elongate axis;
   a first coupling member provided at the proximal end portion of the insertion section and being rotatable on a first pivot in a first direction;
   a handle provided for the first coupling member and rotatable on a second pivot in a second direction perpendicular to the first direction;
   a second coupling member provided for the handle;
   first and second driving rods having first ends and second ends, the first ends being connected to the second coupling member at positions sandwiching the first pivot; and
   a treatment section rotatably connected to the second ends of the first and second driving rods;
   said handle being rotatable from side to side and also being rotatable upward or downward with the first and second pivots as support points,
   said first and second driving rods moving in opposite directions along the elongate axis of the insertion section to rotate the treatment section from side to side when the handle is rotated from side to side about the first pivot, and moving in one direction along the elongate axis of the insertion section to rotate the treatment section up or down, when the handle is rotated up or down about the second pivot.

2. A surgical operation instrument according to claim 1, wherein said insertion section includes a small-diameter pipe, and said first and second driving rods are contained in the small-diameter pipe, extended along the elongate axis of the insertion section, and able to advance or retract along the elongate axis of the insertion section simultaneously or independently.

3. A surgical operation instrument according to claim 1, further comprising another handle which is rotatable upward or downward relative to said handle.

4. A surgical operation instrument according to claim 3, wherein the treatment section includes a pair of jaws which are openable/closable and rotatable from side to side and up and down.

5. A surgical operation instrument according to claim 4, further comprising a third driving rod, which connects one of the jaws to said another handle and allows the jaws of the treatment section to open or close.

6. A surgical operation instrument according to claim 5, wherein, when said another handle is rotated downward relative to said handle, about a third pivot, and becomes parallel to the handle, the third driving rod is retracted, allowing said pair of jaws to close and linearly extend, and allowing said handle and another handle and said pair of jaws to be on the elongate axis of the insertion section.

7. A surgical operation instrument according to claim 5, wherein, when said handle and another handle are rotated upward while maintaining a parallel state, said first and second driving rods are retracted simultaneously along the insertion section, directing said pair of jaws downward in a closed state.

8. A surgical operation instrument according to claim 5, wherein when said handle and another handle are rotated together from side to side, about the first pivot, one of said first and second driving rods is retracted, and another one is advanced, thereby rotating said pair of jaws from side to side.

9. A surgical operation instrument according to claim 5, wherein, when said handle and another handle are opened or closed by rotating said another handle up or down relative to the handle, the third driving rod is advanced or retracted, allowing said pair of jaws to open or close.

10. A surgical operation instrument comprising:
   an insertion section insertable into a body cavity, the insertion section having a distal end, a proximal end and an axis;
   a treatment section provided at the distal end of the insertion section and including a pair of jaws which are openable/closable and which are rotatable relative to the axis of the insertion section;
   an operation section provided at the proximal end of the insertion section, rotatable relative to the axis of the insertion section and including first and second handles which are openable/closable; and
   a driving rod assembly which connects the treatment section and the operation section together and which is advanced or retracted in an axial direction of the insertion section,
   an opening/closing operation of the first and second handles causing an advancing/retracting movement of the driving rod assembly in such a manner as to open/close the jaws of the treatment section, and
   a rotation of the operation section causing the advancing/retracting movement of the driving rod in such a manner as to rotate the treatment section relative to the axis of the insertion section;
   wherein, said first handle is rotatable from side to side relative to a first coupling member, with a first pivot as a support point, and said second handle is rotatable upward or downward relative to the first handle.

11. A surgical operation instrument according to claim 10, wherein said driving rod assembly includes a pair of driving rods, and said first handle is coupled to the treatment section by said pair of driving rods and allows the jaws of the treatment section to rotate from side to side and up and down.

12. A surgical operation instrument according to claim 11, wherein, when the first and second handles are rotated upward while maintaining a parallel state, said pair of driving rods are retracted simultaneously along the insertion section, directing said pair of jaws downward in a closed state.

13. A surgical operation instrument according to claim 11, wherein, when the first and second handles are rotated together from side to side, with a pivot as a support point, one of said pair of driving rods is retracted, and another one is advanced, thereby rotating said pair of jaws from side to side.

14. A surgical operation instrument according to claim 10, wherein said driving rod assembly includes a driving rod, and said second handle is coupled to the treatment section by the driving rod and allows the jaws of the treatment section to open or close.

15. A surgical operation instrument according to claim 10, wherein said driving rod assembly includes a driving rod, and the second handle is rotated downward relative to the first handle, with the second pivot as a support point, and becomes parallel to the first handle, the driving rod is retracted, allowing said pair of jaws to close and linearly extend, and allowing the first and second handles and said pair of jaws to be on the axis of the insertion section.

16. A surgical operation instrument comprising:
   an insertion section including first, second and third driving rods, each having distal and proximal end portions, the insertion section having an elongated axis along the driving rods,
   a pair of jaws;
   a coupling section for connecting the distal end portions of the first to third driving rods to the pair of jaws so that the jaws are open or close, and are rotated in a first plane including the elongated axis and a second plane normal to the first plane, and
   two handles connected to the proximal end portions of the first to third driving rods to move the first driving rod to open or close the jaws, to simultaneously move the second and third driving rods to rotate the jaws in the first plane and to relatively move the second and third driving rods to rotate the jaws in the second plane.

* * * * *